(12) United States Patent
Niermann (10) Patent No.: US 6,537,259 B1
(45) Date of Patent: Mar. 25, 2003

(54) PASSIVE SAFETY DEVICE

(75) Inventor: Volker Niermann, Little Falls, NJ (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 0 days.

(21) Appl. No.: 09/521,078

(22) Filed: Mar. 7, 2000

(51) Int. Cl.[7] .............................. A61M 5/00; A61M 5/32
(52) U.S. Cl. ........................................ 604/263; 604/198
(58) Field of Search .............................. 604/263, 171, 604/192, 198, 110, 164.08, 165.01, 165.03, 240; 128/DIG. 26

(56) References Cited

U.S. PATENT DOCUMENTS

| | | | | |
|---|---|---|---|---|
| 4,790,828 A | * | 12/1988 | Dombrowski et al. | 604/110 |
| 4,955,866 A | | 9/1990 | Corey | 604/192 |
| 5,059,180 A | | 10/1991 | McLees | 604/110 |
| 5,176,655 A | * | 1/1993 | McCormick et al. | 604/192 |
| 5,242,418 A | * | 9/1993 | Weinstein | 604/192 |
| 5,256,152 A | | 10/1993 | Marks | 604/198 |
| 5,295,972 A | | 3/1994 | Michenko | 604/192 |
| 5,328,483 A | | 7/1994 | Jacoby | |
| 5,334,155 A | | 8/1994 | Sobel | |
| 5,549,571 A | | 8/1996 | Sak | 604/198 |
| 5,584,818 A | | 12/1996 | Morrison | 604/197 |
| 5,630,803 A | | 5/1997 | Tamaro | 604/263 |
| 5,688,241 A | | 11/1997 | Asbaghi | 604/110 |
| 5,713,872 A | * | 2/1998 | Isobe | 438/624 |
| 5,735,827 A | * | 4/1998 | Adwers et al. | 604/192 |
| 5,738,665 A | | 4/1998 | Caizza et al. | |
| 5,755,699 A | | 5/1998 | Blecher et al. | 604/198 |
| 5,817,070 A | | 10/1998 | Tamaro | 604/263 |
| 5,833,670 A | | 11/1998 | Dillon et al. | |
| 5,951,525 A | | 9/1999 | Thorne et al. | 604/198 |
| 6,254,577 B1 | | 7/2001 | Huet | |
| 6,261,264 B1 | | 7/2001 | Tamaro | 604/198 |
| 6,375,640 B1 | | 4/2002 | Teraoka | 604/263 |

FOREIGN PATENT DOCUMENTS

| | | |
|---|---|---|
| GB | 2 301 036 A | 11/1996 |
| WO | WO 94/19036 | 9/1994 |

* cited by examiner

*Primary Examiner*—Michael J. Hayes
*Assistant Examiner*—Catherine Serke
(74) *Attorney, Agent, or Firm*—Nanette S. Thomas, Esq.; Scott J. Rittman, Esq.

(57) ABSTRACT

The present invention is a passively shieldable blood collection set. The blood collection set includes a needle cannula, a hub mounted to the needle cannula and a tip guard slidably movable along the needle cannula. The tip guard can be slid into a distal position where the tip of the needle cannula is safely shielded. A collapsible guard drive is mounted to the hub and includes a pair of collapsible leaves extending from the hub to the tip guard. The leaves have a length that enable the tip guard to move into shielding engagement around the tip of the needle cannula, while preventing complete removal of the tip guard from the needle cannula. The leaves are resiliently deformable and can be collapsed onto themselves and onto the hub. The leaves can be retained in their collapsed condition by a packaging cover and subsequently by the grip of a medical practitioner. A mere release of the grip on the collapsed leaves enables the leaves to resiliently return toward an undeflected condition and propels the tip guard distally into shielding engagement around the tip of the needle cannula.

19 Claims, 6 Drawing Sheets

PASSIVE SAFETY DEVICE

BACKGROUND OF THE INVENTION

1. Field of the Invention

The present invention relates to a passively activated safety shield for a needle, such as the needle for an IV infusion set or a blood collection set.

2. Description of the Related Art

A blood collection set or IV infusion set includes a needle cannula having a proximal end, a pointed distal end and a lumen extending therebetween. The proximal end of the needle cannula is securely mounted in a plastic hub with a central passage that communicates with the lumen through the needle cannula. A thin flexible thermoplastic tube is connected to the hub and communicates with the lumen of the needle cannula. The end of the plastic tube remote from the needle cannula may include a fixture for connecting the needle cannula to a blood collection tube or some other receptacle. The specific construction of the fixture will depend upon the characteristics of the receptacle to which the fixture will be connected.

Most needle assemblies include a safety shield that can be moved into shielding engagement with a used needle cannula without risking an accidental needle stick.

Some needle shields are referred to as tip guards, and include a small rigid guard that can be telescoped along the length of a needle cannula. The prior art tip guard may include some form of tether for limiting the travel of the tip guard to the length of the needle cannula. Additionally, the prior art tip guard typically includes structure that lockingly engages over the tip of the used needle cannula to prevent a re-exposure. The structure for preventing re-exposure may include a metallic spring clip or a transverse wall integrally formed with one end of the tip guard.

However, most shields for used needle cannulas require direct manual activation by the medical practitioner.

Therefore, there is a need to provide a passively shieldable needle assembly that will achieve secure shielding of a used needle cannula automatically upon removal of the needle cannula from the patient.

SUMMARY OF THE INVENTION

The present invention is a passively shieldable needle set. The needle set includes a needle cannula having a proximal end, a pointed distal end and a lumen extending therebetween. The needle set further comprises a hub having a proximal end, a distal end and a passage extending between the ends. The proximal end of the needle cannula is securely mounted in the passage of the hub. A flexible tube may be mounted to the proximal end of the hub, such that the passage through the tube communicates with the lumen of the needle cannula. A fixture may be mounted to the end of the tube remote from the hub. The fixture enables the needle cannula and the tube to be placed in communication with an appropriate receptacle, such as a blood collection tube.

The needle set further includes a passive shield assembly. The shield assembly includes an end cap having a blocking surface that is slidably telescoped on the needle cannula for movement from a proximal position where the end cap is substantially adjacent the hub to a distal position where the blocking surface of the end cap surrounds the pointed distal end of the needle cannula. Additionally, the end cap may be configured to prevent proximal movement after the blocking surface of the end cap has advanced sufficiently in a distal direction to protectively enclose the distal tip of the needle cannula.

The end cap may comprise a housing and a protective clip, each of which is formed from a material that is sufficiently hard and rigid to prevent piercing by the distal tip of the needle cannula. The housing may be formed from a thermoplastic material, and the clip may be formed from a metallic material. The clip is configured to be biased against the needle cannula as the end cap moves from its proximal position toward the distal position. However, the clip is further configured to move over the tip of the needle cannula when the end cap is in its distal position.

The passive shield assembly further includes a pair of resiliently deflectable leaves. The leaves have proximal ends that are connected to opposite respective sides of the hub. The leaves further have distal ends connected to opposite respective sides of the tip guard. A portion of each leaf between the respective ends is resiliently collapsible onto itself and into close overlying relationship to the needle hub. Thus, the collapsed leaves can be manually gripped by the medical practitioner to manipulate the needle assembly prior to and during veinipuncture. However, a release of forces on the collapsed leaves enables the leaves to resiliently move toward an undeflected condition in which the leaves extend substantially linearly and parallel to one another on opposed sides of the needle cannula. This resilient unfolding of the leaves transports the tip guard distally along the needle cannula. The leaves have lengths sufficient to enable the tip guard to move into shielding engagement with the tip of the needle cannula, without moving distally beyond the needle cannula.

The needle set further includes a packaging cover having an open proximal end, a distal end, and a generally tubular sidewall extending therebetween. Portions of the sidewall of the packaging cover adjacent the open proximal end are configured to be frictionally mounted over the hub and partially over the collapsed leaves. Thus, the packaging cover functions to hold the leaves in their collapsed condition. The sidewall of the packaging cover is sufficiently long to cover the needle cannula when the proximal end of the packaging cover is mounted to the hub.

A medical practitioner employs the needle set of the subject invention by gripping the collapsed leaves of the shield assembly between a thumb and forefinger at a location proximally of the packaging cover. The packaging cover then is removed, and the tip of the needle cannula is inserted into a blood vessel of a patient. Upon completion of the insertion, the medical practitioner releases the grip on the collapsed leaves, and the leaves begin to unfold due to their inherent resiliency. The unfolding of the leaves causes the tip guard to move distally along the needle cannula. The distal movement of the tip guard will terminate when the tip guard contacts the skin of the patient. After completion of the medical procedure, the practitioner grabs the needle hub or tubing with a thumb and forefinger and pulls the needle cannula from the patient. This relative proximal movement of the needle cannula will permit the leaves to unfold further, thereby moving the tip guard into surrounding relationship to the tip of the needle cannula. The clip or other such structure within the tip guard will prevent a re-exposure of the used needle cannula.

Although the shield assembly is triggered by the medical practitioner, shielding is entirely passive and automatic after the triggering. The triggering action is the release of the collapsed leaves by the medical practitioner. This release can occur after the needle cannula has been placed properly in a blood vessel. Alternatively, this triggering can occur if the needle set is inadvertently dropped. The elapsed time for this shielding will vary depending upon the characteristics of the leaves. Typically, however, complete shielding can occur before a dropped needle has fallen one foot.

DETAILED DESCRIPTION

Figure 1:
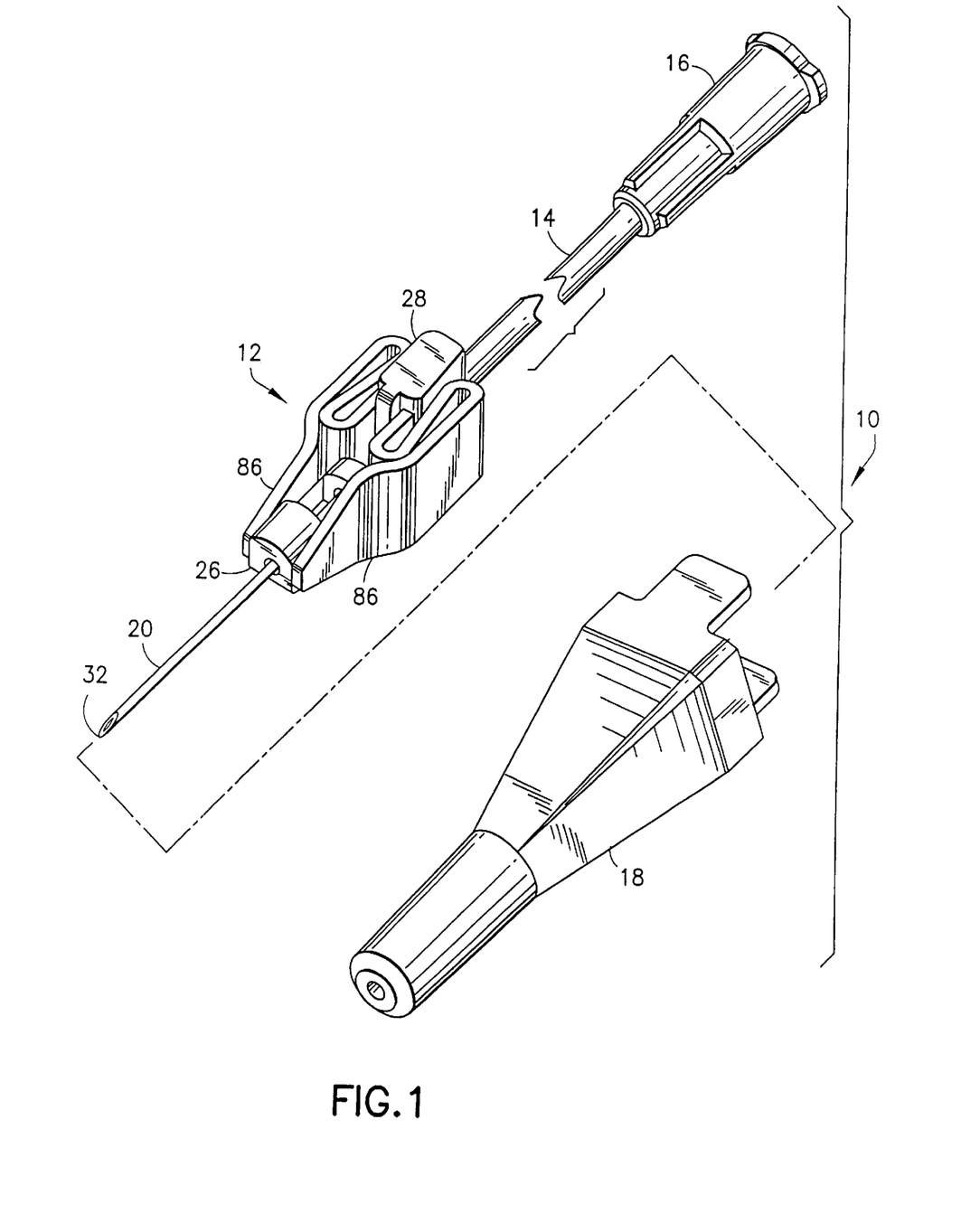
FIG. 1 is an exploded perspective view of a blood collection set in accordance with the subject invention.
Figure 5:
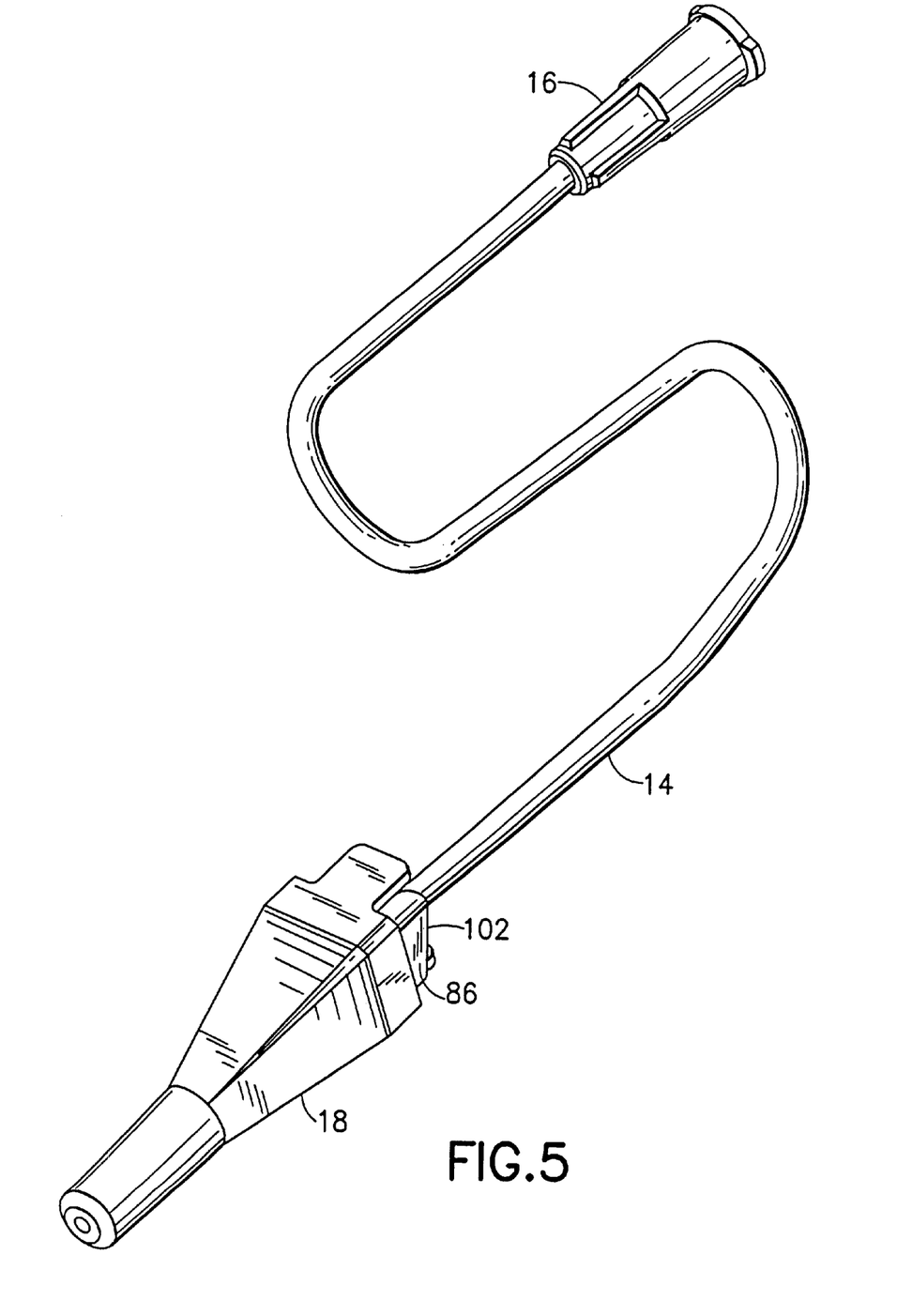
FIG. 5 is a perspective view of the fully assembled blood collection set with the packaging cover thereon.

As shown in FIGS. 1 and 5, blood collection set 10 includes a passively shieldable needle device 12, a flexible tube 14 extending from needle device 12, a fixture 16 mounted to tube 14 and a packaging cover 18 removably mounted to portions of needle device 12 opposite tube 14.

Figure 2:
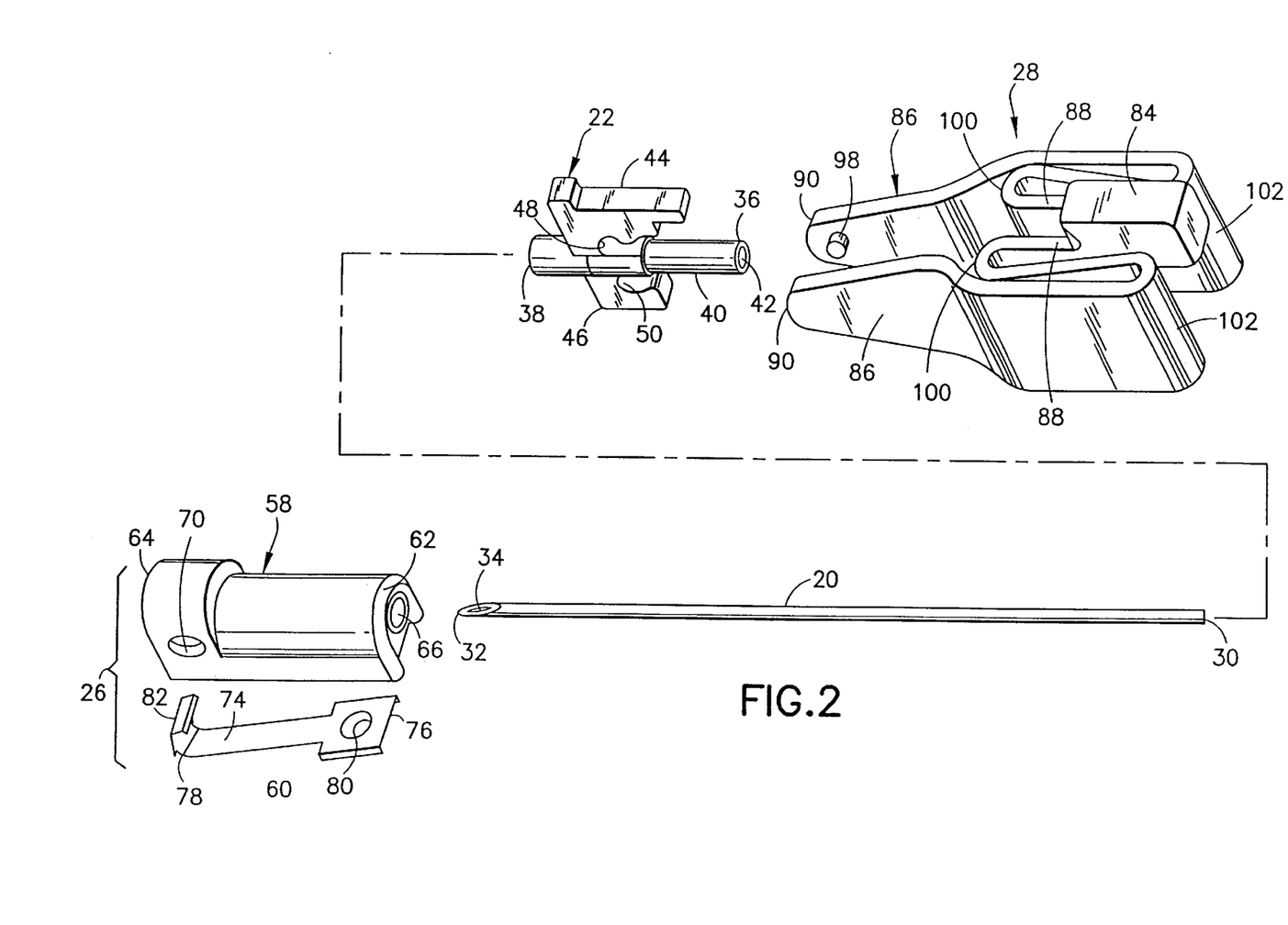
FIG. 2 is an exploded perspective view of the passively shieldable needle device of the blood collection set.
Figure 3:
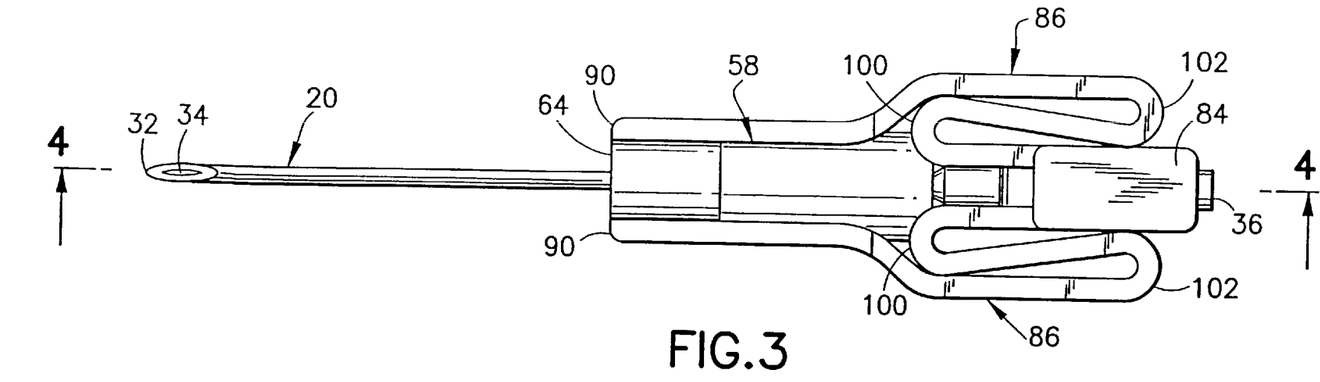
FIG. 3 is a top plan view of the passively shieldable needle device.
Figure 4:
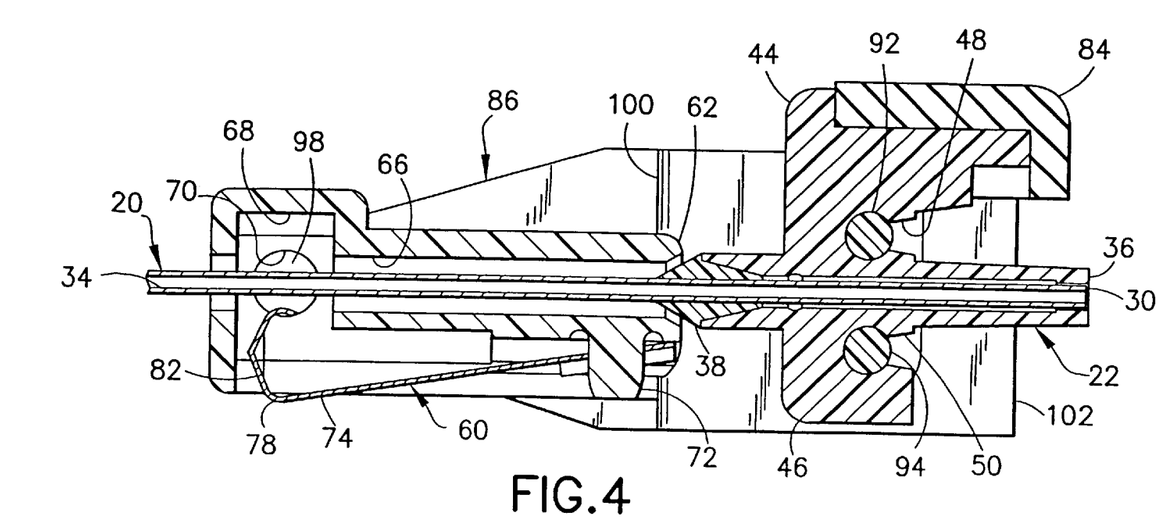
FIG. 4 is a cross-sectional view taken along line 4—4 in FIG. 3.

Passively shieldable needle device 12 of blood collection set 10 as shown in FIGS. 2–4, comprises a needle cannula 20, a hub 22, a tip guard assembly 26 and a collapsible guard drive 28. Needle cannula 20 includes a proximal end 30, a distal end 32 and a lumen 34 extending through cannula 20. Distal end 32 of needle cannula 20 is beveled to define a sharp tip.

Hub 22 is unitarily molded from a thermoplastic material and includes a proximal end 36, a distal end 38 and a rigid tube 40 extending between the ends. Rigid tube 40 is characterized by a passage 42 extending from proximal end 36 to distal end 38 of hub 22. Hub 22 further includes top and bottom flanges 44 and 46 extending oppositely in substantially coplanar relationship from a location on tube 40 approximately midway between proximal and distal ends 36 and 38. The terms top and bottom to identify flanges 44 and 46 are not intended to imply a required gravitational orientation, but do relate to a gravitational orientation that most commonly will be used with blood collection set 10, as dictated by the orientation of the bevel on needle cannula 20.

Top flange 44 of hub 22 is provided with a locking recess 48 substantially adjacent tube 40. Locking recess 48 opens toward proximal end 36 of hub 22 and includes a cross-sectionally reduced entry to enable a snap fit retention of mounting pegs on collapsible guard drive 28, as explained further herein. Similarly, bottom flange 46 includes a locking recess 50 which opens toward proximal end 36 of hub 22 and which has a shape and size substantially identical to locking recess 48.

Needle cannula 20 is positioned in passage 42 of hub 22 and secured by an epoxy, adhesive or the like.

Tip guard assembly 26 includes a housing 58 and a protective clip 60. Housing 58 is unitarily molded from a thermoplastic material and includes a proximal end 62, a distal end 64 and a passage 66 extending between the ends. Portions of passage 66 near distal end 64 define an enlarged clip receptacle 68 as shown in FIG. 4. Symmetrically opposed leaf mounting apertures 70 extend through opposite sides of housing 58 at clip receptacle 68. Additionally, a clip mounting post 72 extends downwardly from housing 58 at a location near proximal end 62 of housing 58.

Clip 60 is unitarily stamped and formed from a resiliently deflectable metallic material. Clip 60 includes a planar spring leg 74 with a proximal end 76 and an opposed distal end 78. A mounting aperture 80 extends through spring leg 74 at a location near proximal end 76. Aperture 80 has a diameter approximately equal to or slightly less than the diameter of mounting post 72 of housing 58. Thus, mounting post 72 can be forced through mounting aperture 80 when the axis of mounting post 72 and the axis of mounting aperture 80 are substantially collinear. A lock out leg 82 extends angularly from distal end 78 of spring leg 74. Lock out leg 82 is bent back toward proximal end 76 of clip 60. The bends in lock out leg 82 enable secure protective engagement with distal tip 32 of needle cannula 20 and further enable smooth sliding movement of tip guard assembly 26 along needle cannula 20 as explained further herein.

Collapsible guard drive 28 includes a downwardly and distally opening mounting block 84 which is dimensioned to slidably engage portions of upper flange 44 of hub 22 furthest from tube 40. Collapsible guard drive 28 further includes a pair of substantially identical leaves 86 extending unitarily from mounting block 84. Each leaf 86 has a width several times greater than the width of needle cannula 20 and a length sufficient to permit shielding of distal end 32 of needle cannula 20 as explained below. Leaves 86 are formed from a resiliently deformable material, such as silicone, that is capable of collapsing onto itself for defining a plurality of folds. Each leaf 86 includes a proximal end 88 and a distal end 90. Proximal end 88 of each leaf 86 is formed with top and bottom locking projections 92 and 94 which extend toward the other of the opposed leaves 86 and which are dimensioned to be lockingly received in locking recesses 48 and 50 of hub 22. Each leaf 86 further includes a distal mounting projection 98 substantially adjacent distal end 90. Distal mounting projections 98 are dimensioned for locking engagement in apertures 70 of tip guard housing 58. Leaves 86 can be folded or collapsed onto themselves and into close overlying relationship with mounting block 84 of collapsible guard drive 28, as shown most clearly in FIG. 2. More particularly, the collapsed folding of each leaf 86 forms distal fold 100 and a proximal fold 102. Proximal folds 102 are disposed substantially in alignment with proximal end 36 of hub 22.

Tip guard assembly 26 is assembled by forcing mounting post 72 of tip guard housing 58 through aperture 80 of clip 60. Spring leg 74 of clip 60, then is urged downwardly or away from passage 66 through tip guard housing 58. Distal end 32 of needle cannula 20 then is urged into passage 66 at proximal end 62 of tip guard housing 58. The downward deflection of spring leg 74 enables distal end 32 of needle cannula 20 to be passed entirely through tip guard 58. Spring leg 74 can be released after tip 32 of needle cannula 20 passes through tip guard housing 58. Thus, the end of lock out leg 82 will be biased against and slide along needle cannula 20. Tip guard assembly 26 then is slid proximally along needle cannula 20 into a position adjacent hub 22.

Mounting block 84 of collapsible guard drive 28 is slid distally over proximal end of top flange 44 on hub 22. This distal movement of mounting block 84 causes projections 94 and 96 of leaves 86 to be lockingly engaged in locking recesses 48 and 50 of top and bottom flanges 44 and 46 respectively. Sufficient distal force will ensure locked engagement of projections 94 and 96 in recesses 48 and 50 of hub 22. Leaves 86 then are collapsed onto themselves as shown in FIGS. 2 and 3 to form distal folds 100 and proximal folds 102. In this collapsed condition, projections 98 on leaves 86 can be aligned with and lockingly engaged in apertures 70 of tip guard housing 58. Leaves 86 are retained in this collapsed condition and packaging cover 18 then is urged proximally over needle cannula 20. With reference to FIG. 1, packaging cover 18 includes an open proximal end configured for frictional engagement over hub 22 an over most of collapsible guard drive 28. However, portions of collapsed leaves 86 adjacent proximal folds 102 are maintained in an exposed state. In this fully mounted condition, distal end 32 of needle cannula 20 is safety disposed within packaging cover 18.

Blood collection set 10 can be packaged substantially in the condition shown in FIG. 5. Prior to use, blood collection set 10 is removed from its package. Fixture 16 then may be connected to an appropriate receptacle for providing communication to lumen 34 through needle cannula 20.

To place needle cannula 20 in communication with a blood vessel, a medical practitioner manually engages proximal folds 102 of leaves 86 at the exposed portions on opposite sides of packaging cover 18. Packaging cover 18 then is urged distally to disengage packaging cover 18 from needle device 12. The medical practitioner then can urge the tip at pointed distal end 32 of needle cannula 20 into a targeted blood vessel of a patient, while continuing to hold collapsed leaves 86 adjacent proximal folds 102 between a thumb and forefinger. After the targeted blood vessel has been accessed, the medical practitioner can release the grip on leaves 86. The inherent resiliency of collapsible guard drive 28 will cause leaves 86 to automatically unfold, thereby propelling tip guard assembly 26 distally along needle cannula 20. Distal movement of tip guard assembly 26 will terminate when distal end 64 of tip guard housing 58 contacts the skin of the patient near the puncture site.

Figure 6:
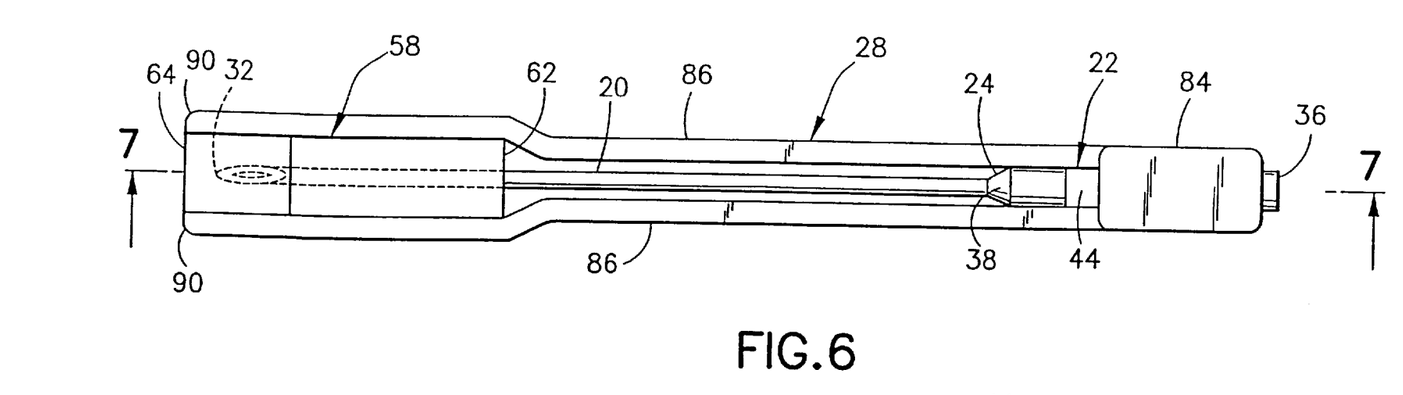
FIG. 6 is a top plan view of the shield assembly in the shielded condition.
Figure 7:
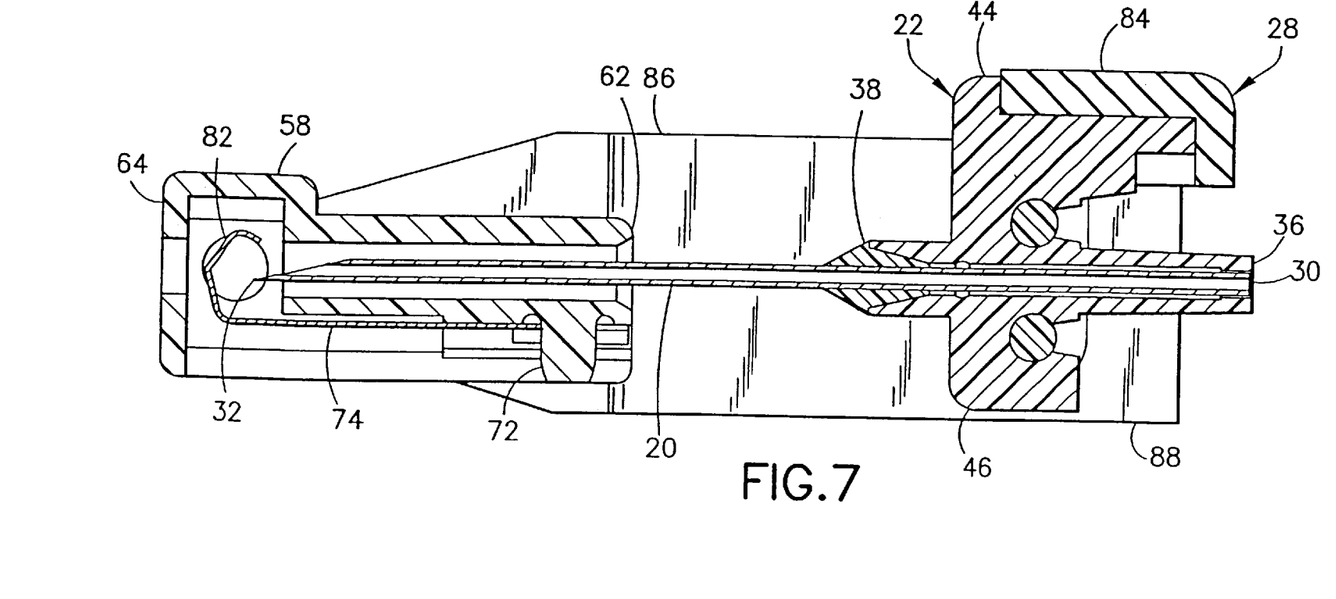
FIG. 7 is a cross-sectional view taken along line 7—7 in FIG. 6.

Upon completion of the required medical procedure, needle cannula 20 is withdrawn from the patient. This removal of needle cannula 20 from the patient will permit further unfolding of leaves 86 and a corresponding distal movement of tip guard assembly 26. After sufficient distal movement of tip guard assembly 26, lockout leg 82 of clip 60 will pass distally beyond tip 32 of needle cannula 20. The inherent resiliency of spring leg 74 of clip 60 will urge lockout leg 82 over tip 32 of needle cannula 20. Thus, a return movement of tip guard assembly 26 that would re-expose the used needle cannula is prevented. Furthermore, leaves 86 have overall length dimensions that will prevent movement of tip guard assembly 26 distally beyond needle cannula 20. Hence, tip 32 of needle cannula 20 is safely shielded. Furthermore, inadvertent contact with portions of needle cannula 20 between the opposed end is substantially prevented by the considerable width of leaves 86 compared to needle cannula, as shown most clearly in FIGS. 6 and 7.

As explained above, the combination of collapsible guard drive 28 and tip guard assembly 26 enables automatic passive shielding of needle cannula 20 merely by removing needle cannula 20 from the patient. In some instances, however, needle device 12 may be dropped or knocked from the hand of the medical practitioner either before veinipuncture or during a medical procedure. The passive shielding described above will commence automatically when needle device 12 is dropped or knocked from the medical practitioner's hand. Thus, the automatic shielding may be triggered by the intentional or unintentional release of the collapsed leaves 86 by the medical practitioner. The speed for this automatic passive shielding will vary in accordance with the materials from which leaves 86 are formed. However, a typical shielding can be completed before needle device 12 falls one foot under the action of gravity.

A medical practitioner does not always enter the targeted blood vessel during the first veinipuncture attempt. However, a medical practitioner typically retains a close grip on the needle device until the targeted blood vessel has been entered. In this instance, the continued gripping of the collapsed leaves 86 will prevent the needle from shielding until the targeted blood vessel has been punctured. The second attempt at accessing a targeted blood vessel generally is a very low risk procedure in which the practitioner's hand is spaced considerably from the tip 32 of needle cannula 20. Thus, blood collection set 10 does not involve the inconvenience of having to use a new blood collection set following each unsuccessful veinipuncture attempt.

Figure 8:
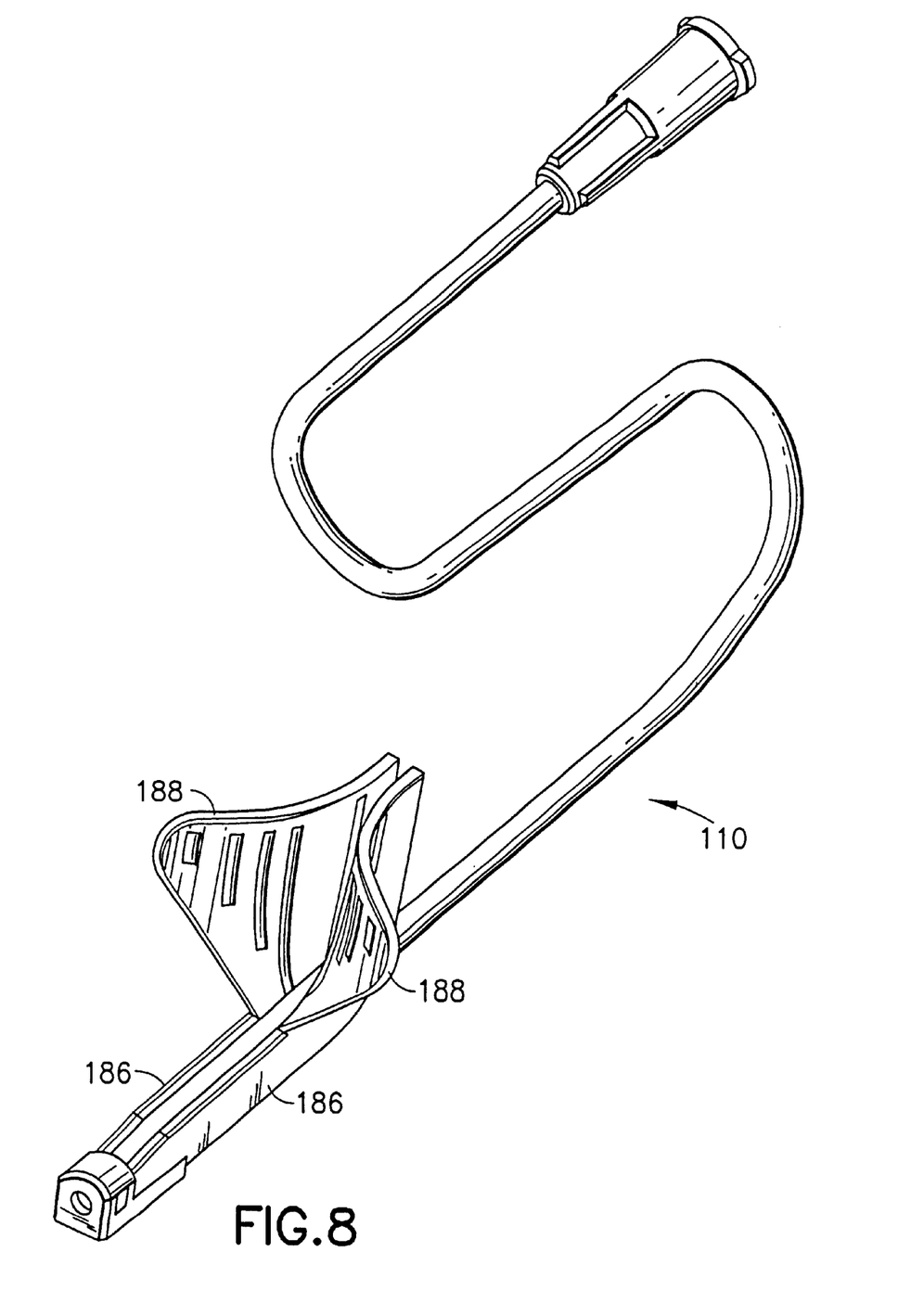
FIG. 8 is a perspective view of a blood collection set showing an alternate shield assembly in shielding engagement around a needle cannula.

FIG. 8 shows an alternate blood collection set 110. Blood collection set 110 is substantially identical to blood collection set 10 described above. However, leaves 186 of blood collection set 110 include wings 188 projecting therefrom. Additionally, a packaging cover used with blood collection set 110 is configured to accommodate wings 188. Wings 188 can facilitate digital manipulation of the shieldable needle device of blood collection set 110.

What is claimed is:

1. A passively shieldable needle device comprising:
   a needle cannula having opposed proximal and distal ends;
   a hub mounted to said proximal end of said needle cannula;
   a tip guard slidably movable along said needle cannula from a proximal position substantially adjacent said hub to a distal position where said tip guard protectively surrounds said distal end of said needle cannula; and
   a collapsible guard drive for propelling said tip guard into said distal position, said collapsible guard drive comprising a pair of resilient deformable leaves, each said leaf having a proximal end connected to said hub and a distal end connected to said tip guard, said leaves being foldable or collapsible onto said hub for retaining said tip guard in said proximal position, said leaves further being resiliently movable toward a non-collapsed condition for propelling said tip guard to said distal position on said needle cannula, wherein said leaves each comprise at least a proximal fold when in said collapsed condition, and wherein with said leaves in said collapsed condition, a plane intersecting said distal end and said proximal fold is substantially parallel to the longitudinal axis of said cannula.

2. The needle device of claim 1, wherein said leaves are formed from silicone.

3. The needle device of claim 1, wherein said leaves are formed of a thermoplastic elastomer.

4. The needle device of claim 1, wherein said leaves are disposed on opposite sides of said needle cannula, said leaves further having a width for substantially preventing contact with portions of said needle cannula between said hub and said tip guard when said leaves have propelled said tip guard into said distal position on said needle cannula.

5. The needle device of claim 1, wherein said collapsible guard drive comprises a mounting block unitary with said proximal ends of said leaves, said mounting block being engageable on said hub.

6. The needle device of claim 5, wherein said hub comprises a plurality of locking recesses formed therein, said leaves having locking projections engageable with said locking recesses on said hub for securely holding said distal ends of said leaves adjacent said hub.

7. The needle device of claim 5, wherein said tip guard comprises a tip guard housing having a plurality of locking apertures formed therein, said distal end of each said leaf having a locking projection securely engaged in one of the locking apertures of the tip guard housing.

8. The needle device of claim 1, wherein the tip guard comprises a tip guard housing formed from a plastic material, a metallic spring clip being mounted to said housing, said spring clip being biased against said needle cannula when said tip guard is in said proximal position and being resiliently moved over said distal end of said needle cannula when said tip guard is in said distal position.

9. The needle device of claim 1, further comprising a detachable retaining element to retain said leaves in said collapsed condition.

10. A passively shieldable blood collection set comprising:
a fixture for connecting said blood collection set to a receptacle;
a flexible tube having opposed first and second ends, said first end of said flexible tube being connected to said fixture;
a hub mounted to said second end of said flexible tube;
a needle cannula having a proximal end connected to said hub, a distal end projecting from said hub and a lumen providing communication to said tube and said fixture;
a tip guard slidably mounted on said needle cannula and movable from a proximal position substantially adjacent said hub to a distal position surrounding said distal end of said needle cannula; and
a collapsible guard drive comprising a pair of resilient collapsible leaves, each said leaf having a proximal end securely connected to said hub and a distal end securely connected to said tip guard, each said leaf further having a length sufficient to permit said tip guard to move from said proximal position to said distal position, said leaves being resiliently collapsible onto said hub, and wherein said leaves each comprise at least a proximal fold when in said collapsed condition, and wherein with said leaves in said collapsed condition, a plane intersecting said distal end and said proximal fold is substantially parallel to the longitudinal axis of said cannula when said tip guard is in said proximal position such that digital squeezing forces on said collapsed leaves retain said tip guard in said proximal position, said leaves resiliently moving toward a substantially linear orientation upon release of said squeezing forces for propelling said tip guard to said distal position.

11. The blood collection set of claim 10, further comprising a packaging cover frictionally engaged on said hub and securely surrounding said needle cannula, such that said packaging cover retains said leaves in said collapsed condition and retains said tip guard in said proximal position, portions of said packaging cover adjacent said hub being configured to permit digital squeezing of said collapsed leaves for retaining said tip guard in said proximal position after removal of said packaging cover.

12. The blood collection set of claim 11, wherein said leaves are formed from silicone.

13. The blood collection set of claim 11, wherein said leaves extend substantially parallel to one another and on opposite respective sides of said needle cannula when said tip guard is in said distal position.

14. The blood collection set of claim 13, wherein the leaves have widths substantially wider than said needle cannula for substantially preventing contact with portions of said needle cannula between said hub and said tip guard when said tip guard is in said distal position.

15. The blood collection set of claim 11, wherein the tip guard comprises a rigid housing having an aperture extending therethrough, said needle cannula being slidably disposed in said aperture, said tip guard further comprising a metallic clip mounted to said housing and configured for sliding engagement against said needle cannula as said tip guard moves from said proximal position toward said distal position, said metallic clip being dimensioned and disposed to protectively cover said distal end of said needle cannula when said tip guard has reached said distal position.

16. The needle device of claim 10, further comprising a detachable retaining element to retain said leaves in said collapsed condition.

17. A passively shieldable needle device comprising:
a needle cannula having opposed proximal and distal ends;
a hub mounted to said proximal end of said needle cannula;
a tip guard slidably movable along said needle cannula from a proximal position substantially adjacent said hub to a distal position where said tip guard protectively surrounds said distal end of said needle cannula; and
a collapsible guard drive for propelling said tip guard into said distal position, said collapsible guard drive comprising a pair of resilient deformable leaves, each said leaf having a proximal end connected to said hub and a distal end connected to said tip guard, said leaves being foldable or collapsible onto said hub for retaining said tip guard in said proximal position, said leaves further being resiliently movable toward a non-collapsed condition for propelling said tip guard to said distal position on said needle cannula,
wherein each said leaf, in said collapsed condition, has a distal fold and a proximal fold, such that portions of said leaves are collapsed onto themselves, and
the needle device further comprising a packaging cover having a generally tubular portion surrounding said needle cannula and having a proximal mounting portion frictionally engaged on said hub, said proximal mounting portion being configured for enabling digital access to portions of said leaves adjacent said proximal folds, whereby said packaging cover retains said leaves in said collapsed condition for holding said tip guard in said proximal position, and whereby said configuration of said proximal end of said packaging cover enables digital gripping of said leaves for retaining said leaves in said collapsed condition and enabling separation of said packaging cover to expose said needle cannula for use.

18. A passively shieldable needle device comprising:
a needle cannula having opposed proximal and distal ends;
a hub mounted to said proximal end of said needle cannula;
a tip guard slidably movable along said needle cannula from a proximal position substantially adjacent said hub to a distal position where said tip guard protectively surrounds said distal end of said needle cannula; and a collapsible guard drive for propelling said tip guard into said distal position, said collapsible guard drive comprising a pair of resilient deformable leaves, each said leaf having a proximal end connected to said hub and a distal end connected to said tip guard, said leaves being foldable or collapsible onto said hub for retaining said tip guard in said proximal position, said leaves further being resiliently movable toward a non-collapsed condition for propelling said tip guard to said distal position on said needle cannula, wherein said collapsible guard drive comprises a mounting block unitary with said proximal ends of said leaves, said mounting block being engageable on said hub, and wherein said hub comprises a plurality of locking recesses formed therein, said leaves having locking projections engageable with said locking recesses on said hub for securely holding said distal ends of said leaves adjacent said hub.

19. A passively shieldable needle device comprising:

a needle cannula having opposed proximal and distal ends;

a hub mounted to said proximal end of said needle cannula;

a tip guard slidably movable along said needle cannula from a proximal position substantially adjacent said hub to a distal position where said tip guard protectively surrounds said distal end of said needle cannula; and a collapsible guard drive for propelling said tip guard into said distal position, said collapsible guard drive comprising a pair of resilient deformable leaves, each said leaf having a proximal end connected to said hub and a distal end connected to said tip guard, said leaves being foldable or collapsible onto said hub for retaining said tip guard in said proximal position, said leaves further being resiliently movable toward a non-collapsed condition for propelling said tip guard to said distal position on said needle cannula, wherein said collapsible guard drive comprises a mounting block unitary with said proximal ends of said leaves, said mounting block being engageable on said hub, and wherein said tip guard comprises a tip guard housing having a plurality of locking apertures formed therein, said distal end of each said leaf having a locking projection securely engaged in one of the locking apertures of the tip guard housing.

\* \* \* \* \*